United States Patent [19]

Sullivan

[11] Patent Number: 5,817,035
[45] Date of Patent: Oct. 6, 1998

[54] BIOPHYSICAL FOETAL MONITOR

[75] Inventor: Colin E. Sullivan, Birchgrove, Australia

[73] Assignee: The Institute of Respiratory Medicine Ltd., New South Wales, Australia

[21] Appl. No.: 836,923
[22] PCT Filed: Nov. 24, 1995
[86] PCT No.: PCT/AU95/00789
§ 371 Date: May 23, 1997
§ 102(e) Date: May 23, 1997
[87] PCT Pub. No.: WO96/15713
PCT Pub. Date: May 30, 1996

[30] Foreign Application Priority Data

Nov. 24, 1994 [AU] Australia ................. PM9640

[51] Int. Cl.⁶ .................................................. A61B 5/02
[52] U.S. Cl. .................................. 600/588; 600/500
[58] Field of Search ........................ 128/660.07, 779, 128/733, 696; 600/453–454, 500, 511, 528, 534, 546, 588

[56] References Cited

U.S. PATENT DOCUMENTS

| | | |
|---|---|---|
| 3,989,034 | 11/1976 | Hojaiban ........................... 128/660.07 |
| 4,256,118 | 3/1981 | Nagel ..................................... 128/733 |
| 4,672,976 | 6/1987 | Kroll ...................................... 128/715 |
| 4,781,200 | 11/1988 | Baker ................................ 128/775 X |
| 5,042,503 | 8/1991 | Török et al. ........................... 128/775 |
| 5,088,497 | 2/1992 | Ikeda ................................. 128/661.07 |
| 5,123,420 | 6/1992 | Paret ....................................... 600/511 |
| 5,257,627 | 11/1993 | Rapoport .......................... 128/661.07 |
| 5,301,680 | 4/1994 | Rosenberg ......................... 128/775 X |
| 5,365,937 | 11/1994 | Reeves et al. ......................... 128/715 |
| 5,373,852 | 12/1994 | Harrison et al. .................. 128/775 X |
| 5,442,940 | 8/1995 | Secker et al. ...................... 600/511 X |
| 5,596,993 | 1/1997 | Oriol et al. ............................ 600/511 |
| 5,609,156 | 3/1997 | Keith et al. ........................ 600/511 X |
| 5,666,959 | 9/1997 | Deans et al. ........................... 600/511 |

Primary Examiner—Francis Jaworski
Attorney, Agent, or Firm—Nixon & Vanderhye

[57] ABSTRACT

A device and method for monitoring over a period of time a foetus in a pregnant mammalian animal. A piezoelectric synthetic plastics material detector is applied to the abdomen of the pregnant animal and produces an electrical signal as a result of foetal activity such as foetal body movement, breathing movement and heart rate. This signal is received in receiver means and is compared with previously determined signals characteristic of various types of foetal activity. Output means produce an output indicative of the activities of the foetus over the monitored period from which can be gauged foetal development and/or well being.

22 Claims, 5 Drawing Sheets

BIOPHYSICAL FOETAL MONITOR

FIELD OF THE INVENTION

The present invention relates to a foetal monitor adapted to report on foetal activity in the womb and to a process for reporting on such foetal activity.

BACKGROUND ART

Foetal development is currently measured in a variety of ways by the midwives and clinicians supervising pregnancy. Current routine measures of foetal development include simple manual methods, such as physical examination by palpation, and auscultation of foetal heart noise; the mother's history, such as date of last menstrual period; the presence or absence of foetal movement ("quickening"); the size of the uterine enlargement; and total maternal weight gain. These have now been supplemented by advanced technological methods. In particular, diagnostic ultrasound provides a high level of information about the foetus providing a "photographic" like real-time image of the foetus which allows the detection of gross physical abnormality. Ultrasound is semi-invasive in that a high frequency soundwave is transmitted into the foetus and the reflected waves are recorded according to how much is absorbed into the foetus or reflected back to the sensor. Although considered safe, there is some uncertainty about potential adverse effect of the ultrasound passing into the foetus.

Ultrasound use has now been extended to develop a clinical "biophysical profile" in which the heart rate is measured, the presence of foetal breathing movements is sought, and then the presence of spontaneous, or evoked (e.g. by manual probing or by externally applied auditory stimuli) foetal body movements. By examining a foetus in this way the attending clinicians are reassured that it is developing normally, or in other cases is identified to be at risk, for example, of placental insufficiency. Although the level of information generated by ultrasound is highly useful and valuable, it provides only, at best a "snapshot" (typically the longest duration being about 20 minutes) of foetus activity in any one day. Such abnormalities as bradycardia and absent foetal breathing movements are used as a guide to the presence of foetal distress, for example from placental insufficiency. In more extreme conditions, the lack of body movements may indicate the possibility of more severe foetal compromise, or even foetal death. The presence of foetal breathing movements are a sign of well-being. At an early stage of any foetal distress, breathing movements cease. The detection of such movements is an important clinical measure of foetal function. However it is known that the foetus has breathing movements in epochs which are usually associated with what is believed to be active wakefulness and in a particular form of sleep called rapid-eye-movement (REM) or "active" sleep. In contrast during quiet non-active wakefulness breathing movements cease, and in non-rapid-eye-movement (NREM) or quiet sleep, breathing movements also cease.

Breathing movements in the foetus do not provide the same function as occurs after birth (i.e. to provide oxygen), as the foetus receives oxygen from the placenta. However, the movements play an important role in the normal development of the lung, and in the training of the breathing muscles, which, after birth must be active continually. Epochs of breathing movement are seen early in the second trimester, when they are scattered throughout the 24 hours in each day. As the foetus matures, it begins to develop a 24 hour rest-activity cycle which is analogous to the infant and adult human sleep-wake cycle. Now, the breathing movements become clustered into epochs of REM sleep, and likely active wakefulness. As these clusterings occur, the epochs of breathing movements occur over longer periods, and the period of their normal absence increase. Thus, a part of the normal foetal maturation includes the development of longer cycle times of rest activity and sleep with consequently longer periods of foetal breathing movements and longer periods of absent breathing movements.

Because diagnostic ultrasound is done over brief periods e.g. 10–20 minutes the likelihood of incorrectly estimating if breathing movements are normal is increased. Although it is possible to do long-term monitoring with ultrasound, the method requires considerable technical skill, and there is the potential risk that the ultrasound may have adverse effects on the foetus. Given the clinical background and the current state of the art, there is a clinical need to provide a safe, reliable and simple method and apparatus to record foetal heart rate, breathing movements and foetal body movements over hours, days and weeks to provide an objective profile of normal foetal development, and to provide a continuous "biophysical profile" on which the clinician can make correct decisions. There is a need to provide this information in the labour ward to monitor the progress of labour, and to provide it at home to give long term information in the weeks and months prior to birth.

It is known from U.S. Pat. No. 5,140,992 to use a piezoelectric plastics material to generate a signal indicative of foetal well being. This specification describes a monitor that detects whether the foetus is, or is not, breathing and whether there is, or is not, a heartbeat.

The present inventor has made the further inventive step of realising that such simple measurements may be utilised in novel ways to produce much more useful outputs.

DISCLOSURE OF THE PRESENT INVENTION

The present inventor has invented a device and a method whereby a foetus may be monitored in a totally non-invasive manner over a period of time and reported on in a new manner that provides significant additional data to the clinician managing the foetus and its mother. The device and the method will provide the midwife, general practitioner, obstetrician or veterinarian with an objective record of foetal development during pregnancy and provides a greatly enhanced method of detecting foetal distress or abnormality.

The present invention consists in a device for monitoring a foetus over a period of time comprising signal processing means having signal receiving means to receive an electrical signal generated by a pressure or acceleration detector applied to the abdomen of a pregnant mammalian animal, the detector being capable of generating an electrical signal representative of foetal activity, comparator means to compare the signal received from the detector with an array of previously determined signals characteristic of a variety of potential foetal activities and output means to produce an output indicative of the activities undertaken by the foetus during that period of time.

In another aspect the invention consists in a method for monitoring a foetus comprising the steps of applying a pressure or acceleration detector to the abdomen of a pregnant mammalian animal for a period of time, producing from the detector an electrical signal representative of foetal activity, comparing the signal so produced with an array of previously determined signals characteristic of a variety of foetal activities and producing an output from that comparison indicative of the foetal activity during that period of time.

While the device and method will normally be used with humans this could be used with equal efficacy to monitor foetal development in other mammalian animals. In horse breeding, for instance, the value of some foals is so high that foetal monitoring is warranted.

In a preferred embodiment of the invention the electrical signal is generated by a piezoelectric transducer or by an accelerometer comprising an integrated circuit containing a floating piezoelectric transducer. The piezoelectric transducer preferably comprises a pair of strips of a synthetic plastics material having piezoelectric properties separated by an insulating layer, more preferably polyvinylidene fluoride (hereinafter called PVDF) or an analogue or family derivative thereof.

The monitoring time is preferably more than one hour, more preferably more than one day, most preferably more than one week. The activities that are likely to be noted are foetal heart rate, foetal breathing movements and foetal body movements. By comparing the signals produced by the detector with an array of signal patterns characteristic of various foetal activities it is possible for the output means to advise the clinicians of such things as the range of activities engaged in by the foetus during the monitored period, the percentage of time that each such activity is engaged, the average duration of each activity and to relate various activities with one another. From this information it is possible to deduce the period of time that the foetus has been engaged in "active" movements, the period engaged in REM "sleep" and the period engaged in non-REM "sleep". These outputs may be compared with typical outputs to aid the clinicians in determining foetal welfare.

A clinician may, for instance, be interested in a decline in heart beat after a period of exercise or a decline in breathing movement after maternal uterine contractions. In either case such an observation may indicate placental insufficiency resulting in the foetus not receiving sufficient oxygen or nutrients. This may lead in the latter stages of pregnancy, for instance to a decision to induce the birth or to conduct a caesarean delivery rather than risk harming the foetus by leaving it in utero.

It is possible for the device according to this invention to detect maternal uterine contractions. The output from the signals generated by such contractions may also supply clinically useful information on its own or when combined with other information gathered by the device. It is known, for instance, that uterine contractions can after exacerbate placental insufficiency. Thus if uterine contractions are followed by signs of foetal distress it may be possible for the clinician to take action to avoid serious compromise to the foetus.

The sensor detects fins movements generated by foetal heart beat, by foetal breathing movements, or by foetal body movements (limb, head, torso) and converts these fine movements into electrical signals. Unlike ultrasound, the sensor is passive, responding to movements generated by the foetus. The electrical signals are filtered and each of the above events separated. Because each of these movements share low frequency components (e.g. 0–11 Hertz), in order to separate the electrical signals each movement (heart, breathing, body) is also characterised by its high frequency components, and this in turn is used to identify which, for example, component of the 0–5 Hertz movement signal is generated by breathing movements, and which is generated by heart movement. A process analogous to the human function of the ear is used to identify the signals. The normal human "ear" (and brain) identifies, characterises, and easily separates noises (for example a human voice) from many different voices in a room and other sources despite the fact that these voices contain a large amount of overlapping sound frequencies. The identity of the voice, which contains mostly overlapping fundamental noise pressure waves, is characterised by "finger print" harmonics for that voice.

The movements generated by the foetus similarly have pressure wave harmonics which permit the separation, identification and then quantification of the breathing movement, heart movement and limb/torso movements. The invention utilises the material PVDF (or a family equivalent) or an integrated microchip amplifier with PVDF as an accelerometer, because this material has a potential frequency response from sub hertz (i.e. less than 1 cycle per second) to kilohertz levels. In addition the material is highly sensitive, producing relatively large voltages in response to extremely small movements. It can, for example act as a highly sensitive microphone detecting low levels of sound pressure. The invention is designed to use this microphone property of PVDF to essentially "listen" to the foetus and to characterise the "sounds" (mostly inaudible to the human ear) which are generated in response to the foetal physiological functions of heart contraction (generating turbulence and heart valve noises), breathing and total body or partial body movement. The invention take advantage of the physical properties of this plastic, which is robust, to characterise the minuscule movements generated by the foetal heart, foetal breathing, and the somewhat larger signals generated by foetal body movement, to identify the dominant frequency components of that movement and, by comparison with each movement's time-linked pressure frequency harmonic profile, to positively separate each from the others thus allowing the generation of an electrical signal which can then be recorded and be identified as that of heart, breathing and body movements.

The electrical signal generated by the foetal physiological movements may then be processed by digital methods (digital signal processors and computers) in real time. Each characteristic movement pressure profile for heart movement, breathing movement, and body movements are identified and then used for continuous monitoring.

Each foetus may have slightly different movement pressure profiles and thus the initial settings of the digital filtering needed to separate the three movement categories will first be verified with simultaneous ultrasound. However, when the range of such profiles is established, the settings of the digital signal filters and the sufficient combination of frequencies and amplitudes which characterise each foetal movement profile will be set permanently in the comparator system, or such defined settings will be used in default mode. With the use of digital recording and large computer memory, the option of recording broad band signals is also available, so that off-line re-analysis of the movement profiles can be undertaken. The sensor configuration may take a number of forms. Direct apposition of the strip of PVDF (e.g. 5–10 cm) against the abdominal surface can be supplemented with an air bubble, or water bubble/bag interface. The latter two formats are available to decrease filtering out of higher frequency components associated with the movements. Another configuration is the direct apposition of a miniaturised accelerometer version of PVDF in which the PVDF material is "floating" inside an integrated circuit microchip amplifier.

In its simplest form the invention consists of a single PVDF sensor held to the abdomen over the foetus by a belt, with two wires coming from the PVDF leading to an amplifier recording system. More complex forms of the invention include more than one sensor, for example on either side, above and below the enlarged uterus. This advanced form of the invention would utilise differing amplitudes of the same "movement profile signature" and so provide a vector identifying the position or area from which the movement was generated. With suitable digital signal processing and computer graphic visual displays, a movement profile map can be generated. This advanced application of the invention will provide additional information about the foetal position and about multiple foetuses.

A further refinement of the invention includes the addition of one or more sensors which are placed away from the foetus on the mother's body. This could include lower side of the thorax, the side of the abdomen, or the back and the upper thigh. Movement signals from these sensors are processed and used by the computer recording system to separate the mother's own breathing, heart and body movements from those generated by the foetus.

The nature of the harness is of importance. A combination of belts is one option. Another option is the use of a close fitting undergarment such as pantyhose or "lycra" tights which comfortably and closely fit over the upper legs, pelvic area and abdomen. In the multisensor version, sensors would be sewn, plastic welded, or inserted into tightly fitting pockets at the desired location. Where maternal breathing and heart movements are to be monitored a body suit version could be used, so that sensors are placed at the rib cage and over the heart.

The amplifier computer processing components of the invention may take a number of formats. The first would be a stand-alone portable box into which is plugged an electrical lead from the sensor. A miniaturised box worn on a belt, analogous to a "Walkman" (Registered Trade Mark) radio is another form to allow ambulatory recording. A miniaturised radio transmitter could be held within a pocket in the belt, harness, or body suit, and transmit (telemeter) the signal to a local receiver.

The record and display could utilise analog and digital recorders and paper hard copies. A preferred method would record digitally on disc for later replay or in real-time on a computer screen. The invention includes software for the display of long-term information.

BRIEF DESCRIPTION OF THE DRAWINGS

Hereinafter, given by way of example only is a preferred embodiment of the present invention described with reference to the accompanying drawings, in which.

BEST MODE OF CARRYING OUT THE INVENTION

Figure 1:
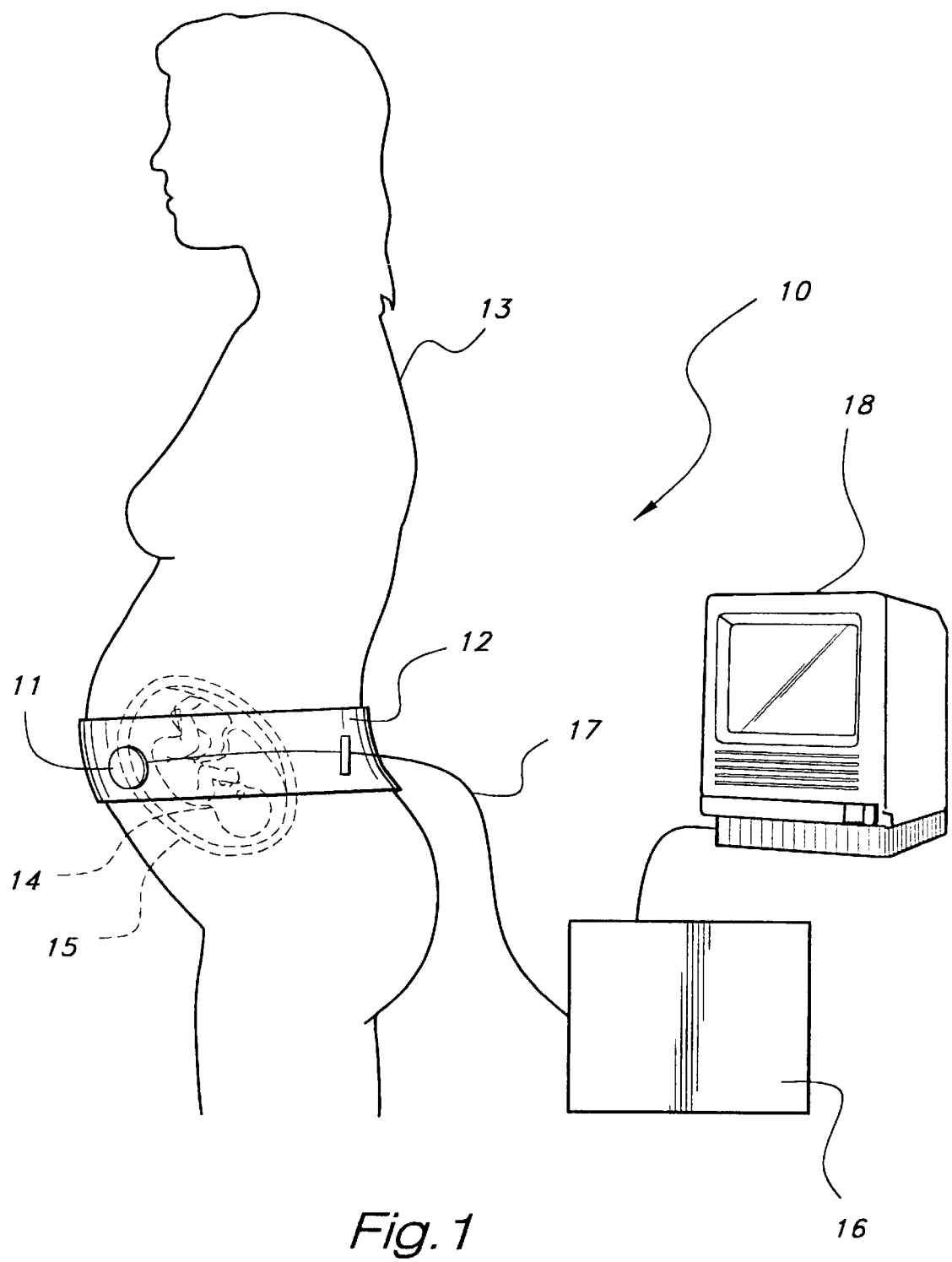
FIG. 1 is a diagrammatic side elevational view of a foetal monitor according to the first embodiment of the present invention.

A device for monitoring a human foetus is generally depicted as 10 in FIG. 1. While adapted to monitor a human foetus, the device 10 could undergo relatively minor modification and be used for the monitoring of the foetus of another mammalian animal, such as a horse.

The device 10 includes a PVDF piezoelectric sensor 11 mounted in a belt 12 wrapped around the waist of the mother 13. In use, the belt 12 is adjusted and tightened so as to position the sensor 11 proximate the position of the foetus 14 in the uterus 15.

The sensor 11 is connected to a processing system 16 by two electrical leads 17 attached between electrodes on the sensor 11 and electrical inputs of the processing system 16. The voltage signals produced by the sensor 11 on the detection of movement by the foetus 14 travel along the leads 17 and are detected by the processing system 16.

The processing system 16 includes an amplifier and a comparator means. The voltage signals are amplified by the amplifier and then compared by the comparator means with an array of previously determined signals characteristic of potential foetal activity including foetal heartbeat, foetal breathing and foetal body movement.

The processing system can also include a digital recording system and computer memory which allow the signals being detected by the sensor 11 to be stored for later play back and analysis by a supervising clinician.

The device 10 in FIG. 1 also has a display means 18 comprising a video display unit into which appropriate signals are supplied by the processing system 16. The display means 18 allows real-time display of the signals being captured by the processing system 16 and so provide for immediate analysis of the wellbeing of the foetus 14.

Figure 2:
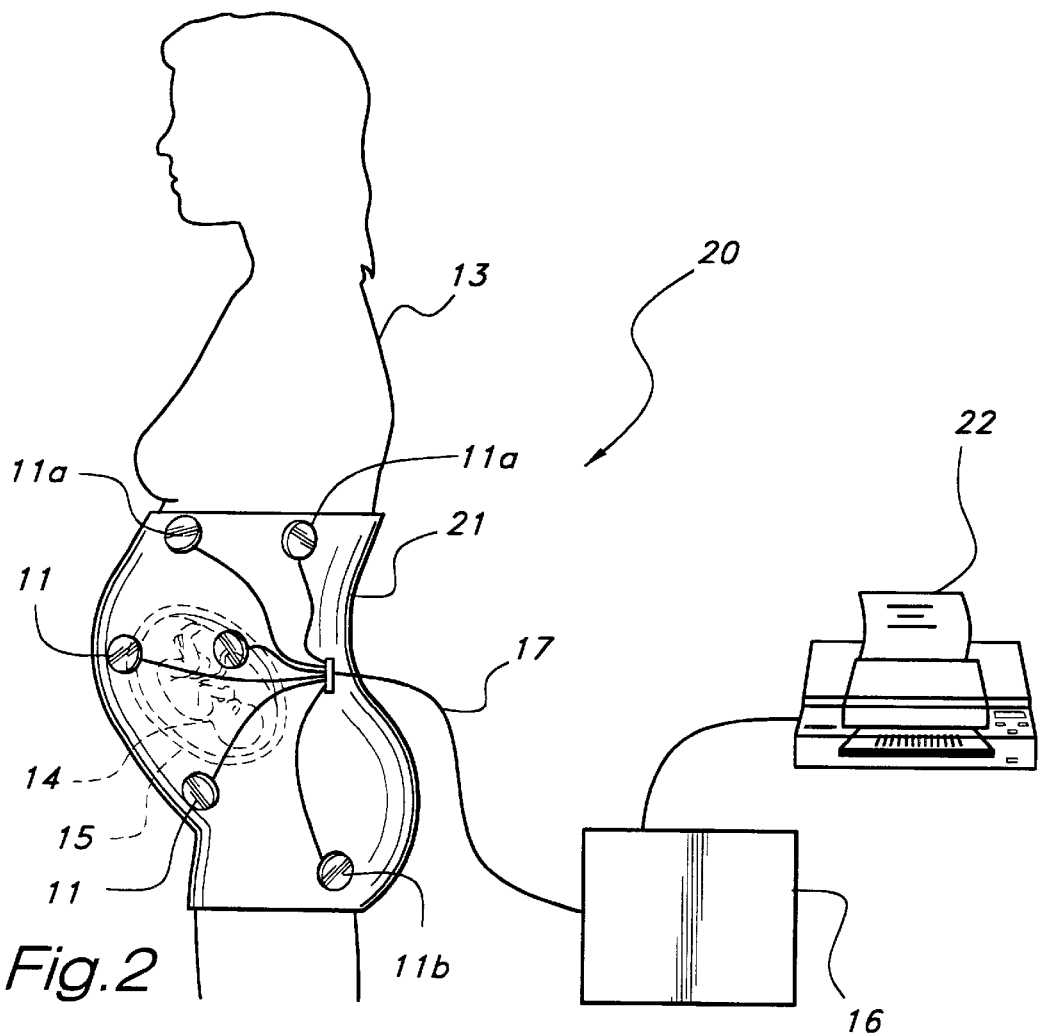
FIG. 2 is a diagrammatic side elevational view of a foetal monitor according to a second embodiment of the present invention.

An alternative device for monitoring a human foetus 14 is generally depicted as 20 in FIG. 2. In this embodiment of the invention, where like features have the same identifying numbers as those given above, the device 20 is adapted to monitor signals from a number of sensors.

The device 20 includes a close-fitting undergarment 21 which comfortably and closely fits over the upper legs, pelvic area, abdomen and rib cage of the mother 13. A number of sensors are sewn into the undergarment 21 such that when the undergarment 21 is fitted to the mother 13 the sensors are appropriately placed on the mother 13. Four sensors 11 are positioned for monitoring the foetus 14 (one on each side, one above and one below the uterus 15) so as to provide a vector identifying the position or area from which a movement has originated. Certain sensors are also positioned so as to detect maternal heartbeat and breathing (sensors 11a) and maternal uterine contractions (sensor 11b).

Electrical leads 17 extend between electrodes oil each of the sensors 11, 11a and 11b and a processing system 16. The processing system 16 comprises an amplifier adapted to amplify the signals received from the sensors 11, 11a and 11b. The processing system is then adapted to utilise the signals detected by sensors 11a and 11b by subtracting corresponding signals produced by the maternal heartbeat or breathing or uterine contractions from the signals produced by the sensors 11 monitoring the foetus 14.

The process signal can then be compared by a comparator means with an array of previously determined signals characteristic of potential foetal activity as previously discussed. The differing amplitudes of the signals generated by the sensors 11 monitoring the foetus 14 would be utilised by the processing system 16 to determine the area or position of the movement being detected.

The device 20 also includes a digital recording system and computer memory which allows the signals being detected by the sensors 11, 11a and 11b to be stored for later playback and analysis. The device 20 also has the display means 22 comprising a printer which records the signals detected by the sensors 11, 11a and 11b for immediate analysis.

Figure 3:
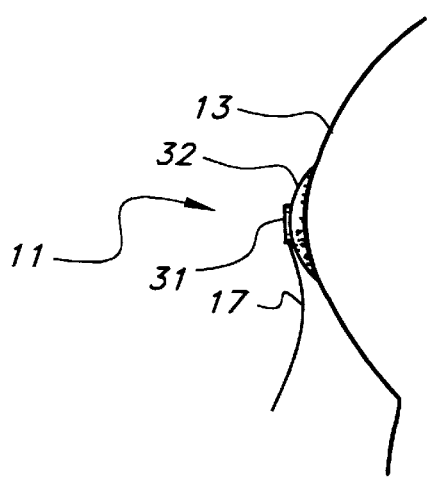
FIG. 3 is a detailed diagrammatic vertical sectional view through a detector for use in the present invention.

As is more clearly depicted in FIG. 3, each sensor 11, 11a or 11b can comprise a PVDF strip 31 attached to a fluid-filled bag 32 which is pressed onto the skin of the mother 13. The fluid-filled bag 32 is used to decrease filtering our of higher frequency components associated with the detected movement.

Both the devices 10 and 20 provide a means of monitoring a foetus 14 over long periods (e.g. greater than 1 day) and so provide a means of determining and monitoring the wellbeing of the foetus 14.

Details of experiments undertaken by the inventor using the invention described herein are provided below.

The aim of the experiments was to determine if it was possible to record a number of indices of foetal physiology with a new non-invasive method using piezoelectric sensors attached to the maternal abdomen over the gravid uterus and capable of detecting fine movements generated by the foetus and foetal physiological function and producing an electrical output.

In particular, the first aim was to determine if it was possible to record signals of sufficient amplitude which could identify foetal body movement, movements generated by foetal heart motion, and movements generated by foetal breathing.

The second aim was to record and display the time sequences and the cross-correlations of the signals generated by different physiological events so as to provide a direct read-out displaying the behavioural states of the foetus.

The third aim was to record these signals over many hours and particularly while the mother was resting and during her entire sleep period and with the simultaneous recordings of a variety of maternally generated physiological events such as maternal body movement, maternal respiration and maternal heartbeat, separate and more clearly define those signals which are generated by the foetus.

The fourth aim was through the use of long-term recordings to display the foetal physiological behaviour over time and to develop a normative "biophysical" profile of the foetus.

The fifth aim was to use the new sensor to identify a "movement profile signature" of specific foetal physiological events. The experiments were designed to determine if such "signatures" could be found, by simultaneously identifying the foetal movement event by a second independent recording method. These "movement signatures" would then form the basis of a memory bank against which on-line recordings would be compared to record the time and number of such events. The aim of these experiments was to use a separate cross referrable indicator of a foetal event (eg the mother's own sense of an event, or the direct visualisation of the foetus by ultra-sound examination), and then provide signal processing of the movement sensor output to define the elements in that signal (eg frequency spectrum, amplitudes etc), which give a reproducible electronic template characterising the event.

A series of sensors were employed in the experiments. The majority were those provided in a special applications designs kit provided by AMP Incorporated, Valley Forge, Pa., USA, through the Australian distributor, Irendos Pty Limited, Glen Iris, Victoria, Australia. Two sensors were used to provide most of the recordings. The first was a sensor manufactured by Irendos Pty Limited as a disposable movement sensor for use on human skin designed to measure eye movements. The second sensor was a device manufactured by Flowscan Inc, Mill Valley, Calif. USA, being a particular configuration of the PVDF material.

A number of standard amplifiers were used in the experiments. The one which was used for most of the experiments was manufactured by Flowscan Inc for use in connection with their particular PVDF sensor.

The unfiltered amplified signal was then passed to a digital recording system having a software selectable processing capability, namely the Amlab System produced by Associative Measurement, North Ryde, New South Wales, Australia.

In order to record a large number of physiological variables simultaneously with the abdominal foetal sensor over a long time interval and then to replay this information for analysis, a multi-channel digital polygraphical recording system was used in the experiments. This system which was supplied by Compumedics Pty Limited, Windsor, Victoria, Australia, provided a platform on which to record all the signals and to permit rapid identification of events for easy replay and analysis.

EXPERIMENT 1

Methods

In a first experiment, four pregnant volunteers underwent a series of afternoon recordings. All subjects were at least 30 weeks pregnant. In one subject, there were five separate afternoon sessions over a number of weeks so that data was obtained between 30 and 39 weeks. In another subject there were two afternoon sessions and in the other subjects single recording sessions were obtained.

The subjects were studied while they lay on a bed. Recordings were obtained with the subject lying in a number of positions, namely supine, left and right lateral posture.

The sensors were placed on the maternal abdomen and were either hand held or taped to the skin. Simultaneously, a mat was placed on the bed under the abdomen. This mat contained a movement sensor which provided a separate output of movement from the mother.

Results

In all subjects, foetal movements were recorded in episodic bursts with a high amplitude in the recording, lasting over periods of 15–30 seconds.

Figure 4:
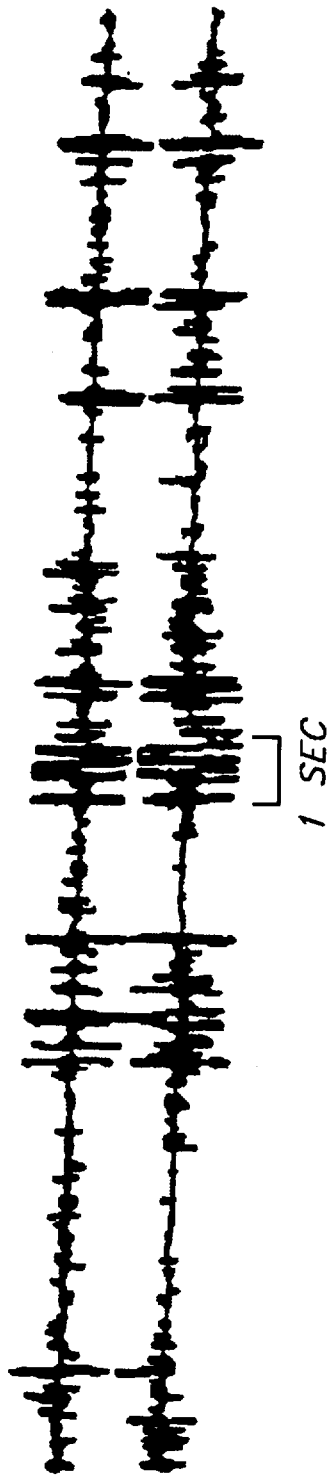
FIG. 4 is an amplitude versus time print-out from a device according to the present invention depicting foetal high amplitude movement.

In many cases, such large movements occurred in bursts, with short silent periods of 15 to 45 seconds (see FIG. 4). These movements were typically felt by the mother. In addition there were periods in which there was mostly stillness. However, during these epochs, there were regular individual large movements which appeared to occur in a fairly regular recurrent pattern separated by 4 to 5 minutes. These epochs of relatively low activity generally lasted over 20 to 30 minutes.

Figure 5:
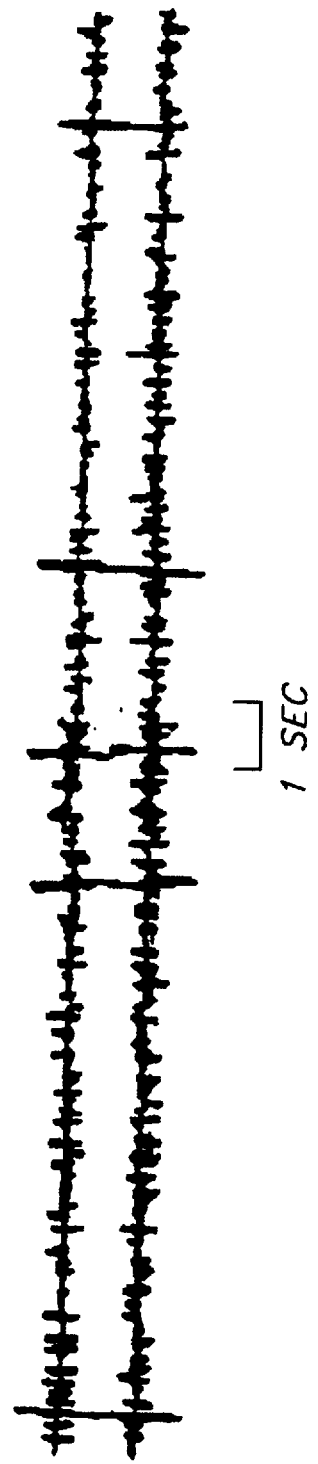
FIG. 5 is an amplitude versus time print-out from a device according to the present invention depicting foetal low amplitude movement.

In addition to the above very obvious movements, there were often periods where short lived twitch-like movements were picked up by the sensor. The amplitude of these movements was clearly lower than those of the longer lasting periods of movement (see FIG. 5). Such movements often occurred repeatedly, but erratically over a long period (for example every 5 to 30 seconds over a 20 to 30 minute epoch). These epochs were distinguishable from periods of longer more intense movement. Characteristically there was a series of short lasting twitches (eg, less than 0.5 seconds in duration), and of small intensity (eg, 50% or less of the characteristic large movement amplitude).

Thus, patterns of movement could be broadly separated into three broad groups:

(1) Movement pattern 1: Epochs where there were high intensity bursts lasting for 5 or more seconds, and as long as 15 seconds. Often, such bursts occurred as a set of bursts over an epoch of time of 5 to 10 minutes.

(2) Movement pattern 2: Epochs where there were brief twitch-like movements, generally of only half the amplitude of the movements described in (1), and of short duration (eg, 0.5 seconds). These twitch-like movements often occurred as a time series with erratic intervals; eg, at 5 to 30 second intervals, the whole sequence lasting for 10 to 20 minutes, in general but longer in some cases.

(3) Movement pattern 3: Epochs with an absence of movements for most of the time. However, there were very regular single large movements. These large movements appear at regular intervals of a number of minutes separation. The whole of these epochs lasted 20 to 30 minutes.

During replay of the recordings, time compression revealed a clear difference in the amplitude of recordings and the two separate epoch patterns where movements occurred could be readily identified visually.

Discussion

The method used in the first experiment provided a ready means of recording foetal movement. In addition, there was clear evidence of a serious of different movement type and intensity/time profiles. There were periods without any movement. There were clear periods of large movements which were prolonged over 5 to 15 seconds, and finally there were periods of fine short duration twitch-like movements.

In previous work by others, four distinct patents of foetal behaviour have been identified using ultrasound (reference: Foetal Behaviour Development and Perinatal Aspects, Ed: Jan G Nijhuis, Oxford University Press, New York, 1992):

State 1F: The foetus is quiescent. There are individual episodes of "startle-like" movements. Eye movements are absent. The foetal heart rate (FHR) is stable, with narrow oscillation bandwidth. Isolated accelerations of FHR do occur, but they are strictly related to the "startle-like" movements. This pattern of FHR is designated pattern A.

State 2F: There are frequent and periodic gross body movements, which are mostly stretches and retroflexion, and movements of the extremities. There is a wider oscillation band width of the FHR (designated pattern B of heart rate), and frequent accelerations of heart rate occur. There are continuous eye movements.

State 3F: There is an-absence of gross body movements, but eye movements are continually present. The FHR is stable, but shows a wider oscillation band width than pattern A, and a more regular oscillation frequency than pattern B. Heart rate accelerations are absent. This is designated FHR pattern C.

State 4F: There is vigorous and continuous activity. There are many trunk rotations, eye movements occur and the FHR is unstable showing long-lasting accelerations: these accelerations often fusing into a sustained tachycardia (FHR pattern D).

These different foetal states are analogous to the new born infant. State 1F is almost certainly equivalent to quiet sleep (or NREM sleep), state 2F is wakefulness, and state 4F is active wakefulness. The new born/infant equivalent to state 3F is active sleep (or REM—Rapid Eye Movement sleep). The only additional state the infant has is state 5F (crying).

A major difference between the foetus and the newborn is the necessity for breathing. The breathing movements stop in foetal state 2F but are present during states 1F, 3F and 4F.

There are some obvious correlations between these previously defined (by direct visual observation with ultrasound recordings) behavioural patterns in the foetus, and the epochs of movement as detected by the surface sensor in the present experiments. This first movement pattern (Pattern 1) corresponds to the 2F state, and likely the 4F state. The third movement found, pattern 3 (minimal movement), likely corresponds to the quiet foetal state 1. Indeed, the occurrence of single large movements occurring at highly regular intervals would seem to closely correlate with the ultrasound defined state 1F where the foetus appears asleep, with the only movements being regular single episodes of stretching.

The most interesting new finding was that there was an apparently new "movement" state identifiable by the presence of fine movements in the surface movement sensor. No similar state has been identified in previous studies. However, it is highly likely that this is the same behavioural state as the 3F state, where the ultra-sound shows continuous rapid eye movements, and an absence of gross body movements. In separate work, it has been shown that the newborn infant has a large number of small body movements (hand twitches, leg twitches) during the active or REM sleep state. It is highly likely that this new movement sensor is detecting such fine body movements in foetal REM sleep. It is also likely that these fine movements are missed by the ultrasound recordings. It is further possible that the fine movements are the result of the rapid eye movements themselves. Regardless of the source, this result strongly suggests that this new movement sensitive recording can provide a better way of detecting the 3F foetal state than is provided by ultrasounds; it clearly provides a non-invasive way of identifying this and other states over long time intervals.

EXPERIMENT 2

Method

In a second separate series of experiments 3 pregnant women were studied while they slept at night. These women were between 32 and 38 weeks pregnant. Full multichannel sleep studies were undertaken using the Compumedic recording system. This system allowed the recording of maternal EEG, eye movements, electromyogram, ECG, respiratory movements, and full body movements.

Foetal movement was recorded with the sensor attached to the maternal abdominal wall.

Results

The subjects in the second experiment were recorded all night from 10pm to about 7am. Normal sleep occurred in each subject Each subject had at least 7 hours sleep. Foetal movement was recorded in all cases. There was a characteristic cyclic pattern of activity. There was a long epoch of the Movement pattern 1 (described above), at the beginning of the study, in each case around 11pm when the mother had been asleep for some hours. Generally there was no prolonged movement for the rest of the night. In each case, however the Movement pattern 1 appeared again about 5am, prior to the mothers awakening from sleep (which usually occurred at 6:30 to 7:00am) Throughout the night there were epochs with movement patterns 2 and 3.

Discussion

These results of the second experiment clearly demonstrated that it was possible to record foetal movement throughout a night of maternal sleep. It also demonstrated that it is possible to record and display the foetal biophysical profile over this long period. It demonstrates that this method will allow the investigation of maternal foetal biorhythm interactions, and provides a means of examining the effects of maternal events on the foetus; for example it will allow the testing of the effects of maternal food intake, the effects of maternal smoking, alcohol, or other medical drug use, on the foetus. The method will be of major use in the testing of the safety of drugs which are required in pregnancy, for example anti-hypertensive drugs.

EXPERIMENT 3

Method

In a third set of experiments foetal heart movement was recorded using the Flowscan sensor. Two subjects were studied, firstly in a series of afternoon studies, and then in all night sleep study. Both foetal movement sensors and heart movement sensors were tested. In a number of experiments electrodes were placed on the maternal abdomen to record foetal electrocardiogram.

Results

Figure 7:
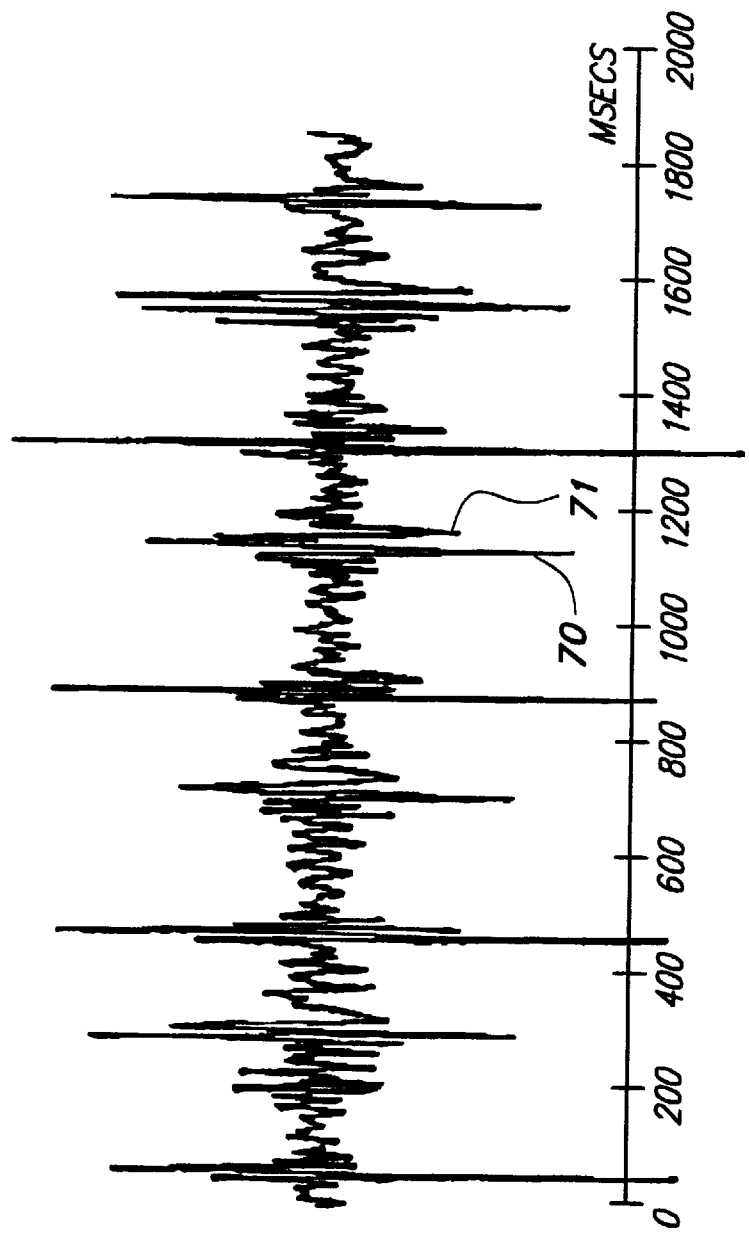
FIG. 7 is an amplitude versus time print-out from a device according to the present invention depicting foetal heartbeat.

In the third set of experiments, the foetal heart was readily detected. A double movement was found which likely corresponds to heart valve opening and closure (see peaks 70 and 71, respectively in FIG. 7). The amplitude of the signal was variable being sensitive to the site of electrode placement. When the foetus moved position, the amplitude changed.

Heart rate accelerations were clearly recognisable in response to foetal movement.

During all night sleep studies, the heart beat was easily recorded throughout the night. When large foetal movement occurred, there was clear acceleration of the heart rate.

Notably, there were long periods where the heart beat signal amplitude remained constant, and then following a large movement, the amplitude lessened, and then remained at a new steady level over long periods. The foetal electrocardiogram could be identified, but in general it was of only a small fraction of the amplitude of the maternal ECG. However, when it was visible, it correlated clearly with the heart movement signal.

Discussion

These results of the third experiment demonstrated that it is possible to record heart impulses continuously with a surface movement sensor. In particular, it was possible to demonstrate the normal heart rate accelerations which occur during foetal movement.

An additional novel finding was that there was a clear change in the amplitude of the signal after some gross foetal movements. This was almost certainly the result of the foetus turning from one side to the other. Because the signal which is produced in the sensor in response to the foetal heart movement is so stable (for example, unlike a bioelectric signals such as ECG or EEG, where change in the electrode resistance occur with time and lead to a change in the signal amplitude which is unrelated to any change in the underlying physiology, (ie electrical recording artefact), the amplitude produced by the heart movement sensor offers important information. Thus by identifying a change in the signal amplitude, it is possible to provide an indication that the foetus has changed positions.

Further, because the sensor signal is detecting movements generated by the mechanical action of the foetal heart, it is likely that it will detect changes in the foetal heart function; for example it is likely the alterations in foetal heart contractility will be identifiable, making this an important diagnostic indicator.

Finally, by measuring the time interval between the foetal electrocardiogram and the heart movement signal (the first beat of which is the aortic valve opening), it will be possible to provide a quantitative index of the circulatory impedance. For example when the placental resistance rises (in placental insufficiency), greater pressure must be developed in the foetal ventricles; this leads to a lengthening of the time interval between the electrical signal (the ECG R trace), and the opening of the aortic valve (the first impulse in the movement sensor).

EXPERIMENT 4

Methods

In a further series of experiments, recordings were made of 4 women during an afternoon session, during which the woman was asked to attempt to identify the particular foetal behaviour.

Each subject was asked to report every sense of foetal activity. A continuous recording of the foetal movement was made using the sensors placed on the maternal abdomen. The experimenter observed the outputs on the video screen of the Amlab system, and each time the mother indicated that there was a foetal event, this was noted with a signal marker on the recording.

Results

All women identified gross and some fine foetal movements. In every case these were displayed simultaneously by the foetal movement sensor. However, there were many more fine foetal movements which were not identified by the mother.

In each case, the mother was able to identify characteristic twitch-like events which occurred as a series. Each volunteered the sense that the foetus was hiccoughing In each case the mother's sense of these events being hiccoughing had been verified on another occasion during routine ultra-sound recordings. These movements showed a characteristic, very large amplitude, but very brief duration twitch. They also tended to occur as a time series at 3 to 5 second intervals.

Discussion

These results of this further series of experiments demonstrated that it was possible to identify by separate means (in this case the mother's own recognition) particular physiological events; eg hiccoughing. The movement pattern in the sensor output was characteristically very high amplitude, but of very short duration. These were unlike any of the other twitch-like phenomena observed, and so were useable as a positive signal identifying the physiological event.

This approach, but using real time on-line ultra-sound, as opposed to simple maternal perception of an event, to identify the event (eg breathing movements, mouthing movements, individual limb movements, urination etc), would form an important method of refining the information contained within the movement signals picked up by the maternal abdominal movement sensor.

Further Experiments

Figure 6:
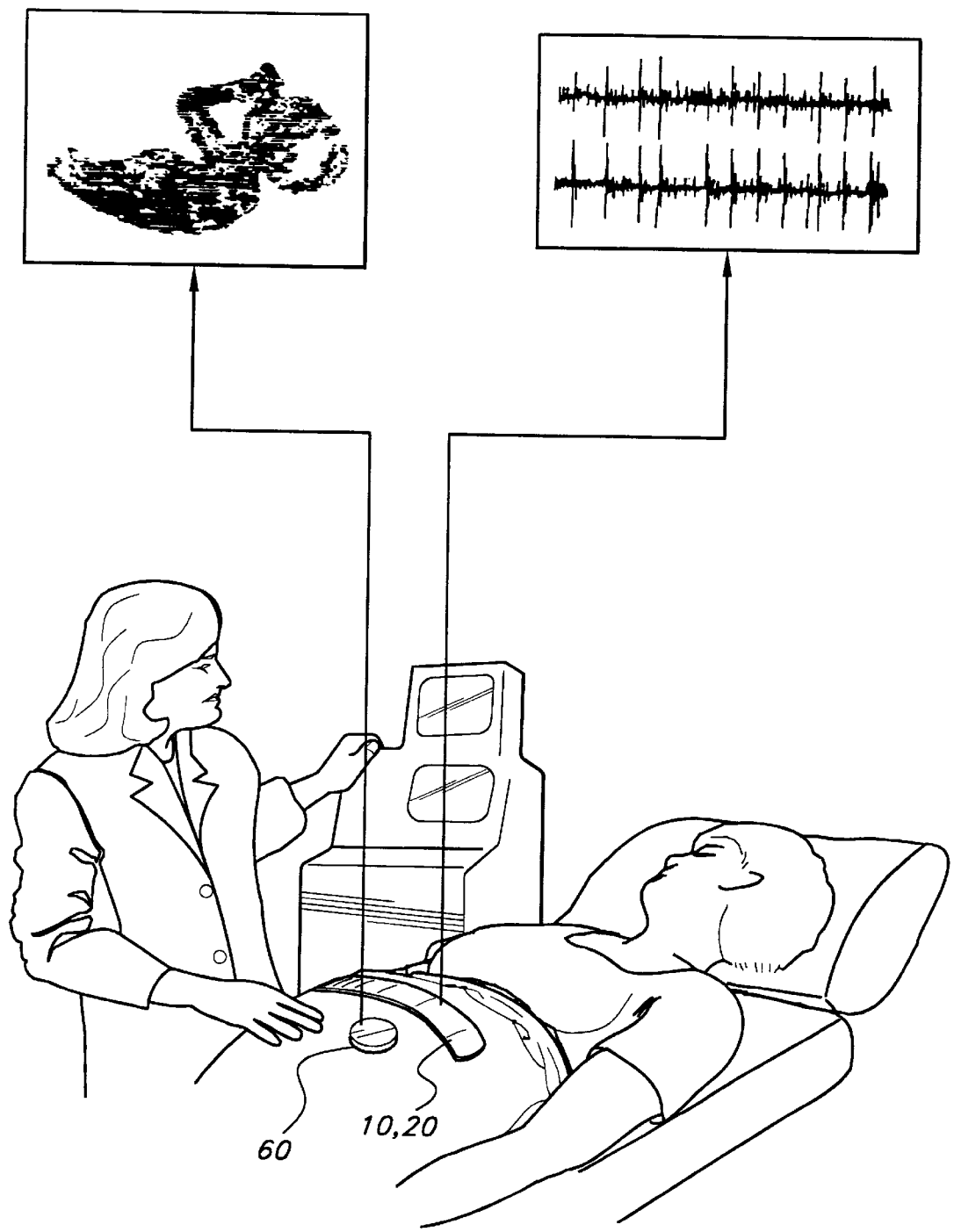
FIG. 6 is a pictorial representation of a patient being monitored by ultrasound and by a device according to the present invention.

It can be seen that in further experiments it will be possible to define, by signal processing the electrical signals of the movement sensors which are generated by a variety of foetal physiological events and movements. In particular, by simultaneously using ultrasound to positively identify a particular event (eg breathing, sucking, mouthing movements, individual arm movements etc), to develop memory banks of particular signals which identify these important individual physiological events. In FIG. 6, the output from an ultrasound sensor 60 is compared with the output from a sensor 10,20 according to the present invention by an operator. This will also include foetal urination, foetal defecation and foetal gut sounds. By producing these particular movement "signatures" it will be possible to use this method to develop full biophysical profiles, and to provide a level of foetal diagnostic information not currently available clinically.

Effects of Uterine Contraction on Foetal Behaviour

It can be seen that this new method of monitoring foetal physiological function can also be used to determine how uterine contraction might compromise the foetus. It is known that uterine contraction can compress the placenta and reduce foetal blood flow, particularly where there is placental insufficiency. This becomes particularly important in the last weeks of pregnancy. The ability to detect foetal bradycardia in response to uterine contraction would provide a useful method of detecting placental insufficiency. A combination of sensors designed to detect foetal movements, heart rate etc, and to simultaneously identify placental contraction will be possible using these new sensor methods.

Placental Blood Flow Measurement

When appropriately tuned to record fine movement, a variation of the new movement sensors will detect signals generated by maternal placental artery blood flow, and placental blood flow itself. When there is partial obstruction of blood flow through any vessel, turbulence occurs; turbulence then produces a considerable amount of pressure energy which is dissipated as vibration of the vessel wall. This vessel wall vibration, in turn dissipates into the surrounding tissues, sending out pressure waves. When appropriately amplified and tuned, abnormal placental blood flow is recordable on the maternal abdominal wall. When these measures are combined with the other signals of foetal function a comprehensive monitoring device for tracking the well-being of both the mother and foetus will be possible. By the early identification of placental insufficiency, and in turn the early signs of foetal distress, appropriate intervention can be undertaken, for example early delivery, or, in some cases suppression of uterine contraction and delaying of labour.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

I claim:

1. A device for determining the types of movement of a foetus over a period of time, comprising:

a pressure or acceleration detector means for application to a pregnant mammalian animal and for producing a stream of electrical signals in response to the detection of foetal movements;

signal processing means having signal receiving means for receiving the stream of signals produced by the detector means;

comparator means for comparing the stream of signals received by the signal receiving means with an array of previously determined streams of signals characteristic of a variety of different types of identified foetal movement to allow determination of the type or types of foetal movement occurring during the period of time; and output means for producing an output indicative of the types of movement of the foetus during the period of time.

2. The device a claimed in claim 1 in which the signal processing means is connected directly to the pressure or acceleration detector means.

3. The device as claimed in claim 2 in which the detector means is selected from the group consisting of a pressure detector comprising a piezoelectric transducer and an accelerometer comprising an integrated circuit containing a floating piezoelectric transducer.

4. The device as claimed in claim 3 in which the piezoelectric transducer is a pair of strips of a piezoelectric synthetic plastics material separated by an insulating layer.

5. The device as claimed in claim 4 in which the piezoelectric synthetic plastics material is polyvinylidene fluoride (PVDF).

6. The device as claimed in claim 4, in which the piezoelectric transducer is mounted on one side of a fluid filled container which may be applied on its other side to the abdomen of a pregnant mammalian animal.

7. The device as claimed in claim 1 in which the signal processing means is connected directly to relay means for relaying a broad band signal derived from the pressure or acceleration detector means.

8. The device as claimed in claim 1 in which the signal receiving means includes an amplifier.

9. The device as claimed in claim 1 in which the signal receiving means includes means for removing unwanted signals.

10. The device as claimed in claim 1 in which the comparator means contains previously determined streams of signals characteristic of foetal movements selected from the group consisting of foetal breathing movements, gross foetal body movement, foetal eye movement, foetal hiccoughing, and foetal heartbeat.

11. The device as claimed in claim 1 in which the comparator means further contains previously determined streams of signals characteristics of maternal uterine contractions.

12. The device as claimed in claim 1 in which the signal receiving means receives streams of signals from a plurality of detector means.

13. The device as claimed in claim 12 in which the signal receiving means receives signals from both the detector means and additional detector means placed on the body of the pregnant animal.

14. The device of claim 13 wherein the detector means is placed on the abdomen of the pregnant animal and the additional detector means are placed on the pregnant animal at sites other than on the abdomen.

15. The device as claimed in claim 14 in which the signal processing means includes means for utilizing the signals received from the additional detector means to remove unwanted signals produced by the detector means on the animals abdomen.

16. A device for determining the types of movement of a foetus over a period of time, comprising:

a pressure or acceleration detector for application to a pregnant mammalian animal and for producing a stream of electrical signals in response to the detection of foetal movements;

a signal processor having a signal receiving device for receiving the stream of signals produced by the detector;

a comparator for comparing the stream of signals received by the signal receiving device with an array of previously determined streams of signals characteristic of a variety of different types of identified foetal movement to allow determination of the type or types of foetal movement occurring during the period of time; and an output device for producing an output indicative of the types of movement of the foetus during the period of time.

17. A method for determining the types of movement of a foetus over a period of time including the steps of:

applying a pressure or acceleration detector means, capable of producing a stream of electrical signals in response to the detection of foetal movements, to a pregnant mammalian animal for a period of time;

comparing the stream of electrical signals produced by the detector means with an array of previously determined streams of signals characteristic of a variety of different types of identified foetal movement to allow determination of type or types of movement occurring during the period of time; and producing an output from that comparison indicative of the types of movement of the foetus during the period of time.

18. The method as claimed in claim 17 in which the foetus is monitored for a period of time of at least one hour continuously.

19. The method as claimed in claim 18 in which the foetus is monitored for a period of time of at least one day substantially continuously.

20. The method as claimed in claim 19 in which the foetus is monitored for a period of time of at least one week substantially continuously.

21. The method as claimed in claim 20 in which the stream of signals produced by the detector means is compared with previously determined streams of signals characteristic of foetal movements selected from the group consisting of foetal breathing movements, gross foetal body movement, foetal eye movements, foetal hiccoughing and foetal heartbeat.

22. The method as claimed in claim 21 in which the stream of signals produced by the detector means is further compared with previously determined streams of signals characteristic of maternal uterine contractions.

\* \* \* \* \*